(12) United States Patent
Nishino

(10) Patent No.: US 8,610,894 B2
(45) Date of Patent: Dec. 17, 2013

(54) DRYNESS FRACTION MEASURING DEVICE AND DRYNESS FRACTION MEASURING METHOD

(75) Inventor: Giichi Nishino, Tokyo (JP)

(73) Assignee: Azbil Corporation, Tokyo (JP)

( * ) Notice: Subject to any disclaimer, the term of this patent is extended or adjusted under 35 U.S.C. 154(b) by 194 days.

(21) Appl. No.: 13/313,265

(22) Filed: Dec. 7, 2011

(65) Prior Publication Data
US 2012/0147375 A1 Jun. 14, 2012

(30) Foreign Application Priority Data

Dec. 10, 2010 (JP) ................................. 2010-275953

(51) Int. Cl.
*G01N 21/00* (2006.01)
*G01J 3/42* (2006.01)
(52) U.S. Cl.
USPC ............................ 356/437; 356/432; 356/320
(58) Field of Classification Search
USPC .................................................. 356/432–444
See application file for complete search history.

(56) References Cited

U.S. PATENT DOCUMENTS

| | | | | |
|---|---|---|---|---|
| 4,137,462 A | * | 1/1979 | Wyler | 250/573 |
| 4,716,360 A | * | 12/1987 | Pakulis | 324/640 |
| 5,020,000 A | * | 5/1991 | Carmichael | 702/30 |
| 6,128,079 A | * | 10/2000 | McCloskey et al. | 356/338 |
| 7,034,302 B2 | * | 4/2006 | Davidson et al. | 250/339.1 |
| 7,037,554 B2 | * | 5/2006 | Tao et al. | 427/163.2 |
| 7,381,954 B2 | * | 6/2008 | Banerjee et al. | 250/339.1 |
| 8,141,412 B2 | * | 3/2012 | Chen et al. | 73/29.01 |
| 2009/0101822 A1 | * | 4/2009 | Mitra et al. | 250/339.1 |
| 2009/0248306 A1 | * | 10/2009 | Terychnyi et al. | 702/6 |

FOREIGN PATENT DOCUMENTS

| | | |
|---|---|---|
| JP | 8-312908 A | 11/1996 |
| JP | 2000-121616 A | 4/2000 |

* cited by examiner

*Primary Examiner* — Gregory J Toatley
*Assistant Examiner* — Jarreas C Underwood
(74) *Attorney, Agent, or Firm* — Troutman Sanders LLP

(57) ABSTRACT

The provision of a dryness fraction measuring device includes a light-emitting body for irradiating moist steam with light of a plurality of wavelengths; a light-receiving element for receiving light of the plurality of wavelengths that has traversed the moist steam; and a dryness fraction calculating device for calculating the dryness fraction of the moist steam based on the received light intensity at each of the plurality of wavelengths.

11 Claims, 10 Drawing Sheets

200
DRYNESS FRACTION MEASURING DEVICE AND DRYNESS FRACTION MEASURING METHOD

CROSS REFERENCE TO RELATED APPLICATIONS

The present application claims priority under 35 U.S.C. §119 to Japanese Patent Application No, 2010-275953, filed Dec. 10, 2010, which is incorporated herein by reference.

FIELD OF TECHNOLOGY

The present invention relates to a measuring technology, relating to a dryness fraction measuring device and dryness fraction measuring method.

BACKGROUND

After water reaches its boiling point, it becomes moist steam that is a mixture of water vapor gas (the gas phase part) and water droplets (the liquid phase part). Here the weight ratio of the water vapor gas relative to the moist steam is termed the "dryness fraction." For example, if water vapor gas and water droplets exist at half each, the dryness fraction would be 0.5. Moreover, when there are no water droplets but instead there is only water vapor gas, then the dryness fraction would be 1.0. From the perspective of efficiency of use of the sensible heat and latent heat within the moist steam in heat exchanging equipment, and the like, from the perspective of preventing corrosion of turbine blades in steam turbines, and so forth, it is desirable that the dryness fraction of the moist steam be brought to near 1.0. Because of this, a variety of methods have been proposed whereby to measure the moist steam.

For example, Japanese Unexamined Patent Application Publication H8-312908 ("JP '908") discloses a technology for calculating the dryness fraction by calculating the saturated hydraulic enthalpy and the saturated steam enthalpy using a saturated steam table based on the dry steam flow rates and pressures before and after a pressure regulating valve, taking advantage of the fact that there is no change in total enthalpy across a pressure regulating valve that is disposed in a pipe. Moreover, Japanese Unexamined Patent Application Publication 2000-121616 ("JP '616") discloses a technology for calculating the dryness fraction based on acoustic velocity through the provision of a branch flow pipe in a pipe and the provision of ultrasonic receiver within the branch flow pipe.

However, in the technology disclosed in JP '908, high accuracy dryness fraction measurements are difficult, considering the complexity of the structure, and the increasingly large compounding tolerances due to the need to provide a plurality of flow rate sensors and pressure sensors.

The technology disclosed in JP '616 requires the provision of a branch pipe, requiring great care in the installation. Moreover, it requires expensive ultrasound receiving equipment able to endure the high temperature and high pressure environment. Moreover, while acoustic velocity and dryness fraction are correlated, pressure also has an effect on the dryness fraction, and thus a separate pressure sensor is required as well.

Given this, one object of the present invention is the provision of a dryness fraction measuring device and dryness fraction measuring method whereby the dryness fraction can be measured accurately and easily.

SUMMARY

An example is summarize as being a dryness fraction measuring device having (a) a light-emitting body 11 for irradiating moist steam with light of a plurality of wavelengths; (b) a light-receiving element for receiving light of the plurality of wavelengths that has traversed the moist steam; and (c) a dryness fraction calculating device for calculating the dryness fraction of the moist steam based on the received light intensity at each of the plurality of wavelengths.

Another example is summarized as being a dryness fraction measuring method including: (a) irradiation of moist steam with light of a plurality of wavelengths; (b) reception of light of the plurality of wavelengths that has traversed the moist steam; and (c) calculation of the dryness fraction of the moist steam based on the received light intensity at each of the plurality of wavelengths.

The present invention enables the provision of a dryness fraction measuring device and dryness fraction measuring method whereby the dryness fraction can be measured accurately and easily.

DETAILED DESCRIPTION

Examples of the present invention will be described below, in the descriptions of the drawings below, identical or similar components are indicated by identical or similar codes. Note that the diagrams are schematic. Consequently, specific measurements should be evaluated in light of the descriptions below. Furthermore, even within these drawings there may, of course, be portions having differing dimensional relationships and proportions.

Figure 1:
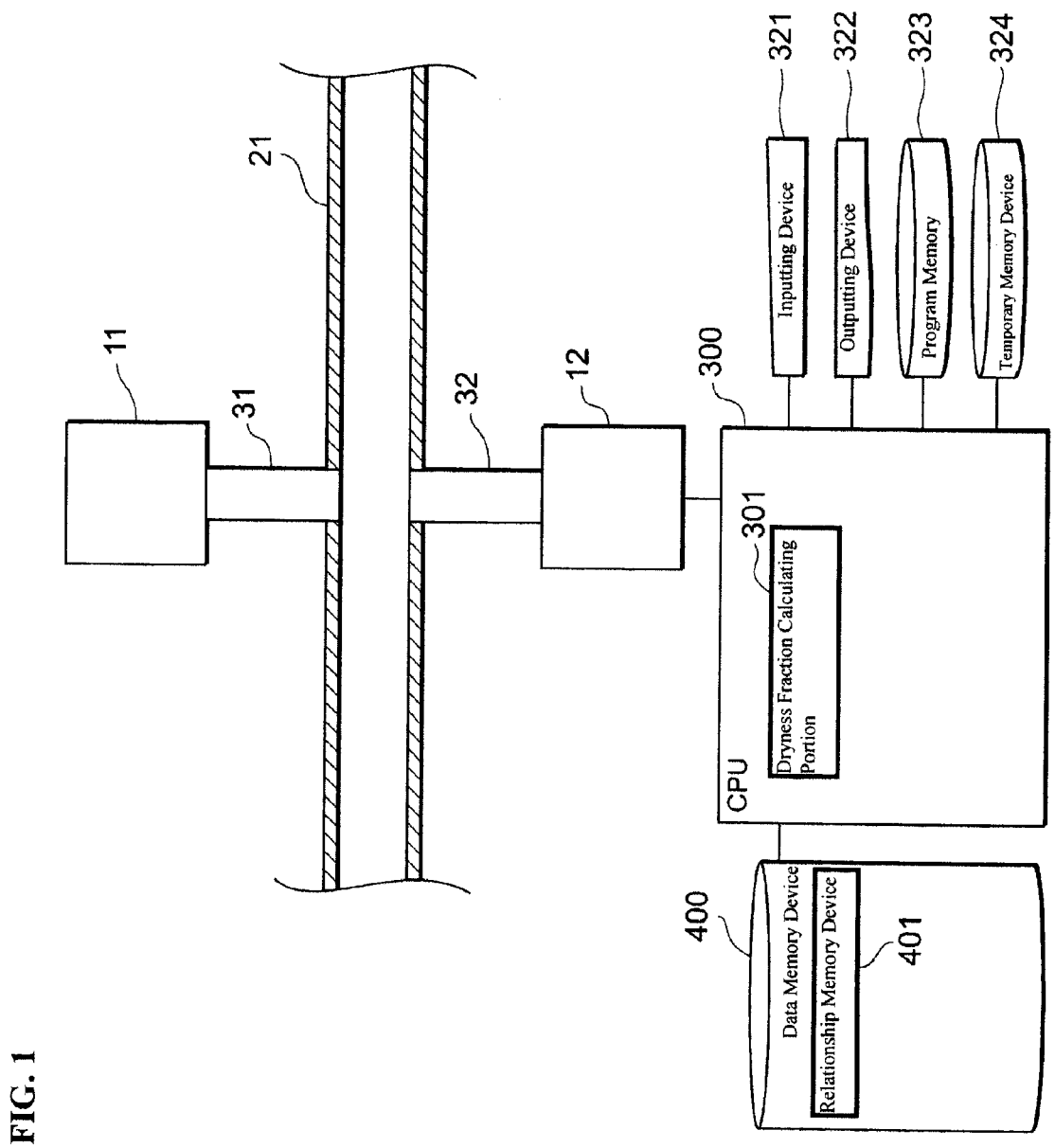
FIG. 1 is a schematic diagram illustrating a dryness fraction measuring device according to an example.

A dryness fraction measuring device, as illustrated in FIG. 1, includes a light-emitting body 11 for irradiating moist steam with light of a plurality of different wavelengths; a light-receiving element 12 for receiving light of the plurality of wavelengths that has traversed the moist steam; and a dryness fraction calculating device 301 for calculating the dryness fraction of the moist steam based on the received light intensity at each of the plurality of wavelengths.

Figure 2:
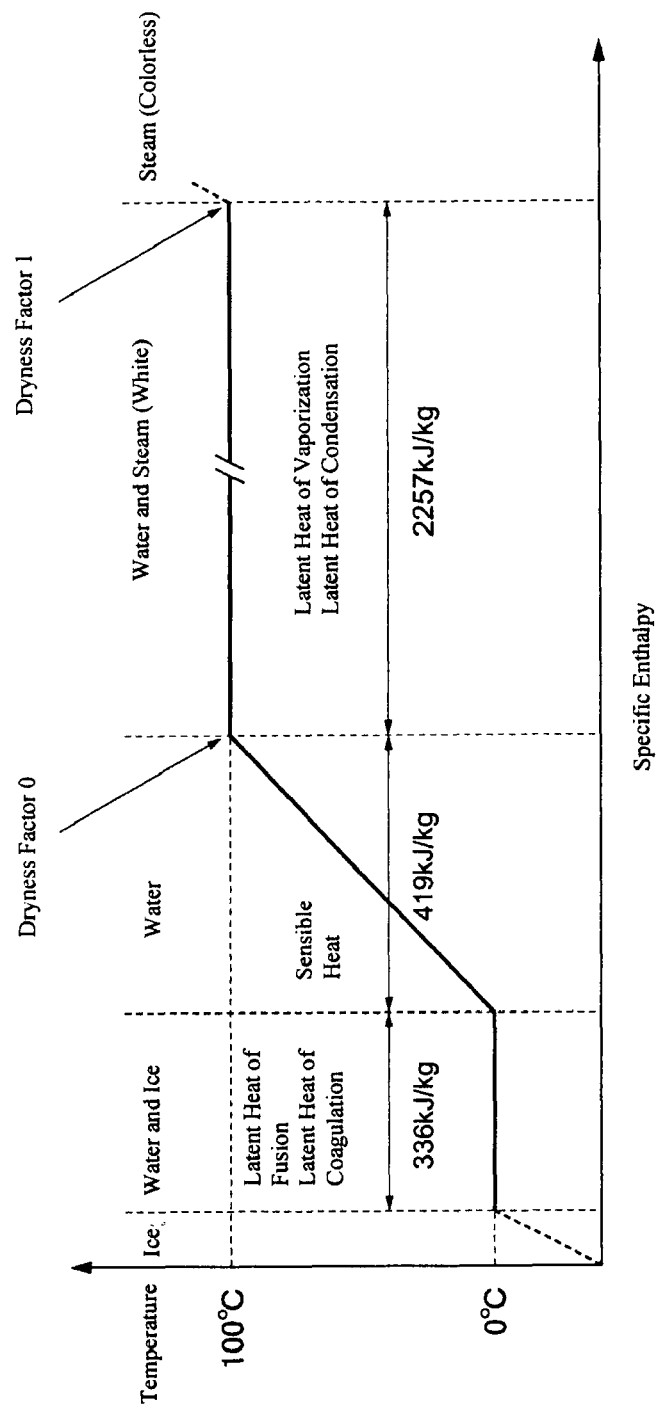
FIG. 2 is a graph illustrating a state change in moisture at atmospheric pressure in a further example.

As illustrated in FIG. 2, after water reaches its boiling point, it becomes moist steam wherein water, as liquid droplets, and steam are mixed to be in a coexisting state. Here the ratio of the vapor gas relative to the total weight of the moist steam is termed the "dryness fraction." Consequently, saturated vapor has a dryness fraction of 1, and saturated liquid has a dryness fraction of 0. Conversely, the dryness fraction is also defined as the ratio of the difference between the moist steam specific enthalpy and the saturated liquid specific enthalpy, relative to the latent heat specific enthalpy.

Figure 3:
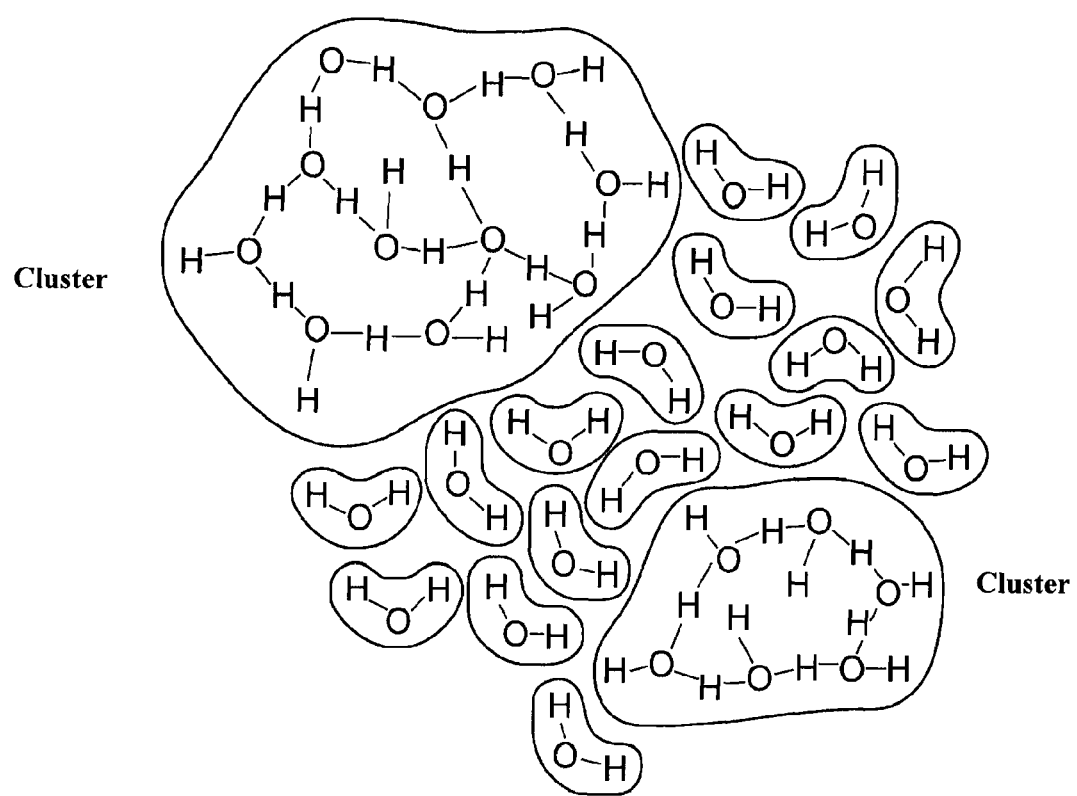
FIG. 3 is a schematic diagram of a water molecule duster according to an example.
Figure 4:
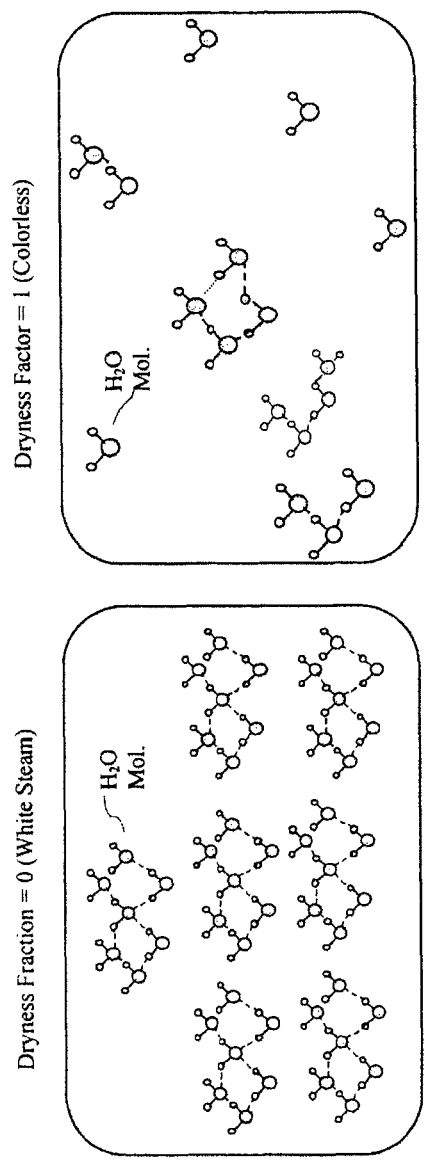
FIG. 4 is a schematic diagram illustrating the state of a water molecule depending on the dryness fraction according to another example.
Figure 5:
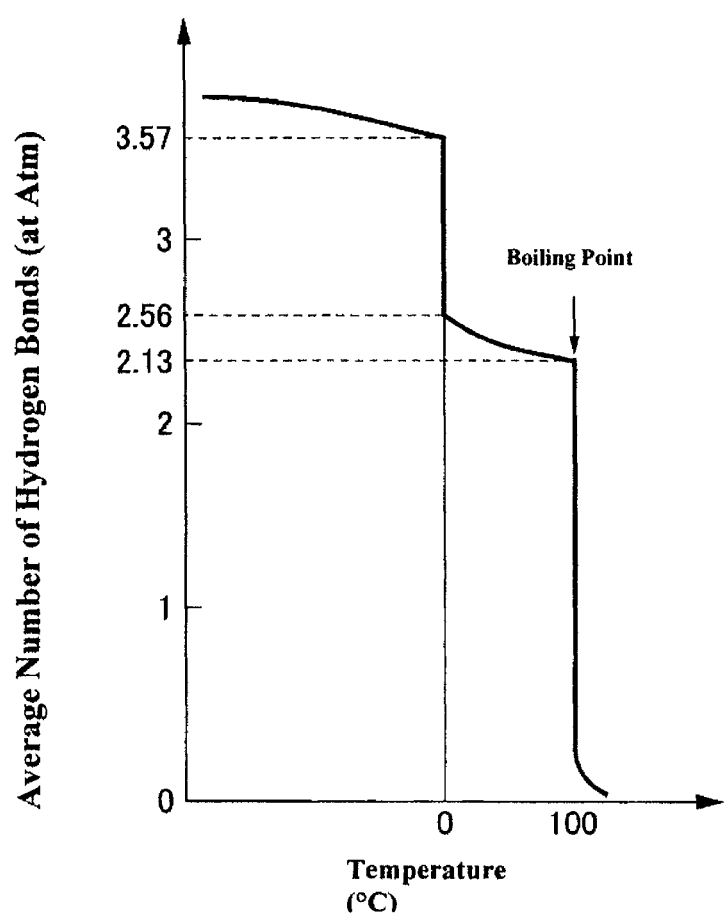
FIG. 5 is a graph illustrating an example of the relationship between temperature and the average hydrogen bond count of a cluster of water molecules in another example.

Water undergoes phase changes through differences in the numbers of hydrogen bonds that are formed between the water molecules. In the moist steam, the water molecules bond together through hydrogen bonds to form clusters as illustrated in FIG. 3. As illustrated in FIG. 4 and FIG. 5, the average number of hydrogen bonds in a cluster in moist steam with a dryness fraction of 0 at atmospheric pressure is, for example, 2.13. The average number of hydrogen bonds in a cluster falls as the dryness fraction approaches 1, where there tends to be an increase in the water molecules that exist singly.

Figure 6:
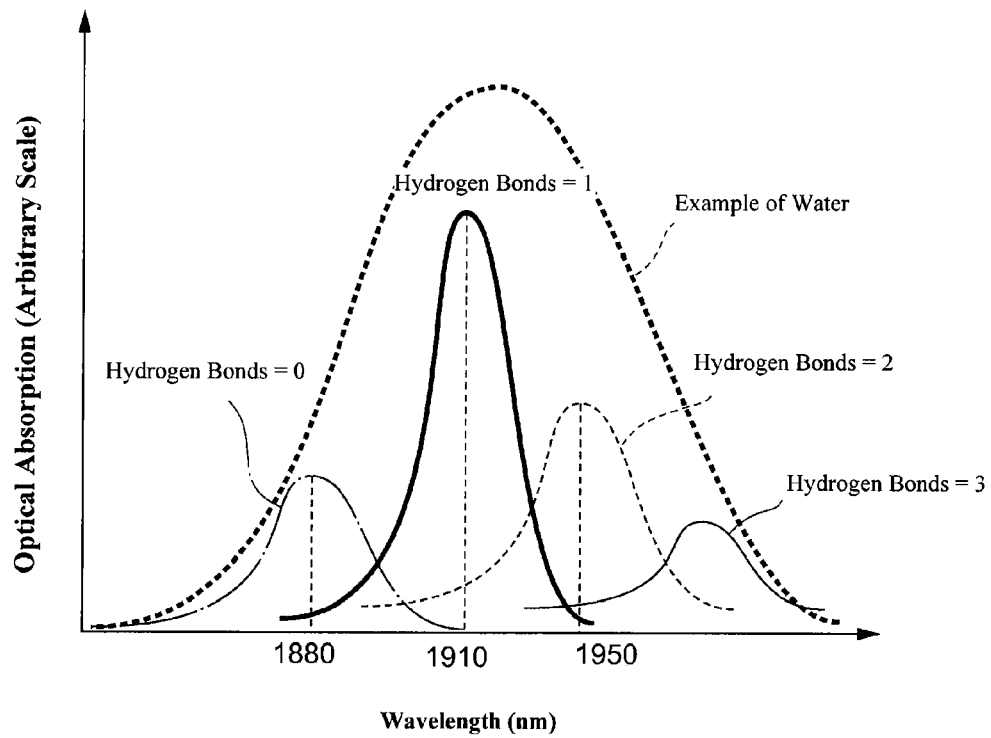
FIG. 6 is a graph illustrating an example of the water molecule absorption spectrum according to yet another example.
Figure 7:
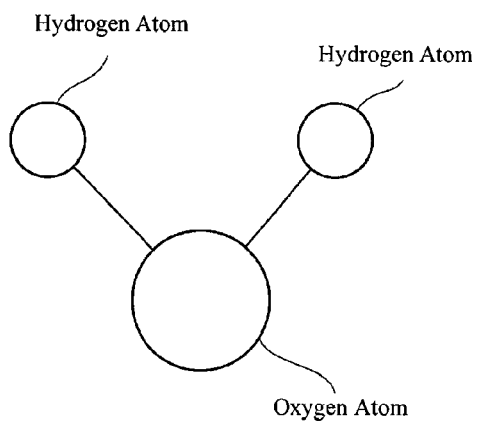
FIG. 7 is a schematic diagram of a water molecule that exists singly according to a further example.
Figure 8:
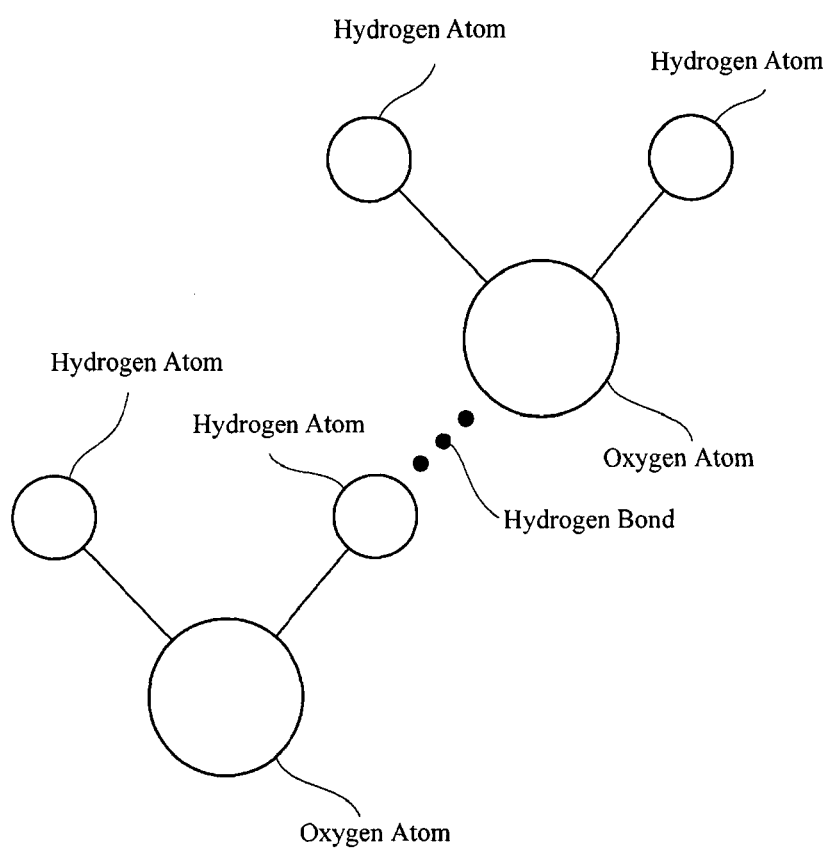
FIG. 8 is a schematic diagram of a two water molecules that are bonded by a single hydrogen bond according to an example.
Figure 9:
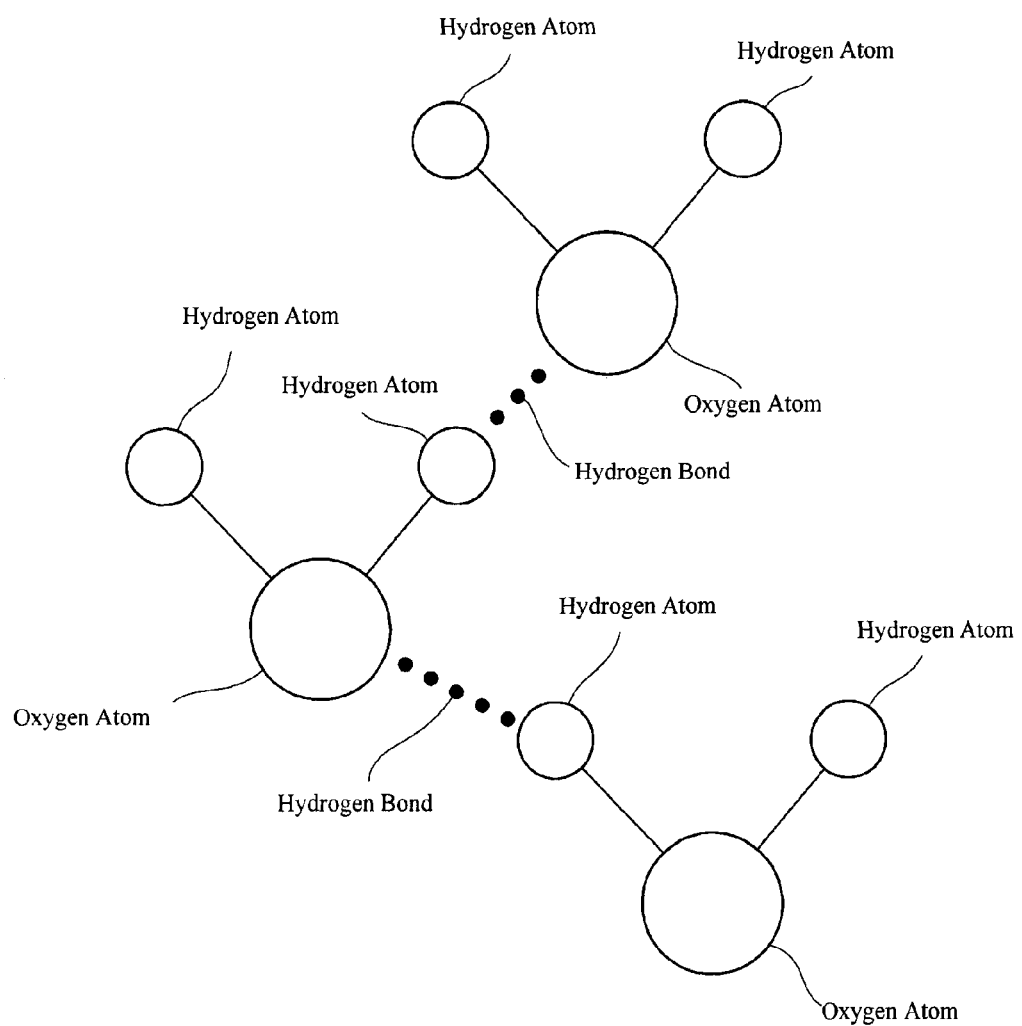
FIG. 9 is a schematic diagram of a three water molecules that are bonded by two hydrogen bonds according to another example.

FIG. 6 is an example of an exertion spectrum exhibited by water molecules. As illustrated in FIG. 7, the water molecules that exist singly provide an absorption spectrum that has peaks at 1840 and 1880 nm. As illustrated in FIG. 8, the water molecules wherein two water molecules are bonded by a single hydrogen bond provide an absorption spectrum that has a peak at 1910 nm. As illustrated in FIG. 9, the water molecules wherein three water molecules are bonded by a two hydrogen bonds provide an absorption spectrum that has a peak at 1950 nm, in general, the greater the number of hydrogen bonds included in a cluster formed by water molecules the longer the wavelength of the peak of the absorption spectrum.

In FIG. 1, the dryness fraction measuring device is connected to a pipe 21 through which moist steam passes. The light-emitting body 11 produces light at least two different wavelengths. For example, one of these at least two different wavelengths is the 1880 nm wherein the absorption peak for water molecules appears when the number of hydrogen bonds is zero, and the other wavelength is the 1910 nm wherein the absorption peak of water molecules appears when the number of hydrogen bonds is 1. In this way, the light that is produced by the light-emitting body 11 is set so that the degrees of optical absorption of each of the plurality of wavelengths is correlated to the number of hydrogen bonds that are formed between the water molecules in the cluster.

The light-emitting body 11 may be provided with a plurality of light-emitting elements emit lights of different wavelength. Conversely, the light-emitting body 11 may emit light of a broad wavelength band. A light-emitting diode, a superluminescent diode, a semiconductor laser, a laser oscillator, a fluorescent discharge tube, a low-pressure mercury lamp, a xenon lamp, a label, or the like, can be used as the light-emitting body 11.

An optical waveguide 31 is connected to the light-emitting body 11. The optical waveguide 31 carries the light that is produced by the light-emitting body 11 into a pipe 21. For example, the optical waveguide 31 passes through a side wall of the pipe 21. Conversely, an optically transparent window may be provided in the side wall of the pipe 21, and the optical waveguide 31 may be connected to the window. The light that is carried by the optical waveguide 31 enters into the pipe 21 from the end portion of the optical waveguide 31. While plastic optical fibers made out of poly methyl methacrylate (PMMA), glass optical fibers made out of quartz glass, or the like, may be used in the optical waveguide 31, there is no limitation thereto insofar as it is capable of carrying the light that is produced by the light-emitting body 11.

If the light-emitting body 11 emits, for example, at least light with a wavelength of 1880 nm and light with a wavelength of 1910 nm, then, the light with the wavelength of 1880 nm will, within the pipe 21, be absorbed by the water molecules that exist singly that are included in the moist steam. Moreover, light with the wavelength of 1910 nm will be absorbed by the water molecules wherein two molecules are bonded by a single hydrogen bond within the moist steam. As described above, the average number of hydrogen bonds there are within the water molecule cluster falls as the dryness fraction goes from 0 to 1. Consequently, there is a tendency for the light with the wavelength of 1880 nm to be absorbed more, and the light with the wavelength of 1910 nm to be absorbed less, as the dryness fraction of the moist steam within the pipe 21 goes from 0 to 1.

An optical waveguide 32 into which enters light that has traversed the pipe 21 is connected to the pipe 21. The optical waveguide 32 guides, to the light-receiving element 12, the light that has traversed the moist steam within the pipe 21. An end portion of the optical waveguide 32 faces an end portion of the optical waveguide 31. Moreover, the optical waveguide 32 passes through a side wall of the pipe 21. Conversely, an optically transparent window may be provided in the side wall of the pipe 21, and the optical waveguide 32 may be connected to the window.

Note that the light-emitting body 11 may be disposed in the side wall of the pipe 21 to eliminate the optical waveguide 31. Moreover that the light-receiving element 12 may be disposed in the side wall of the pipe 21 to eliminate the optical waveguide 32. Moreover, while in FIG. 1 the light-emitting the 11 and the light-receiving element 12 face each other, a light-emitting/light-receiving element wherein the light-emitting body 11 and the light-receiving element are integrated together may be used instead. In this case, a reflecting plate is disposed on the side wall of the pipe that faces the light-emitting/light-receiving element. The light that is produced by the light-emitting/light-receiving element passes through the interior of the pipe and is reflected by the reflecting plate, to be received by the light-emitting/light-receiving element.

A photodiode, or the like, may be used for the light-receiving element 12. Note that in the case wherein the light-emitting body 11 emits light of a broad wavelength band, a filter that transmits only at least two different wavelengths may be disposed in front of the light-receiving element 12. For example, the light-receiving element 12 received, at least, the 1880 nm light that is most absorbed by the water molecules when the number of hydrogen bonds is 0, and the 1910 nm light that is most absorbed by the water molecules when the number of hydrogen bonds is 1.

Figure 10:
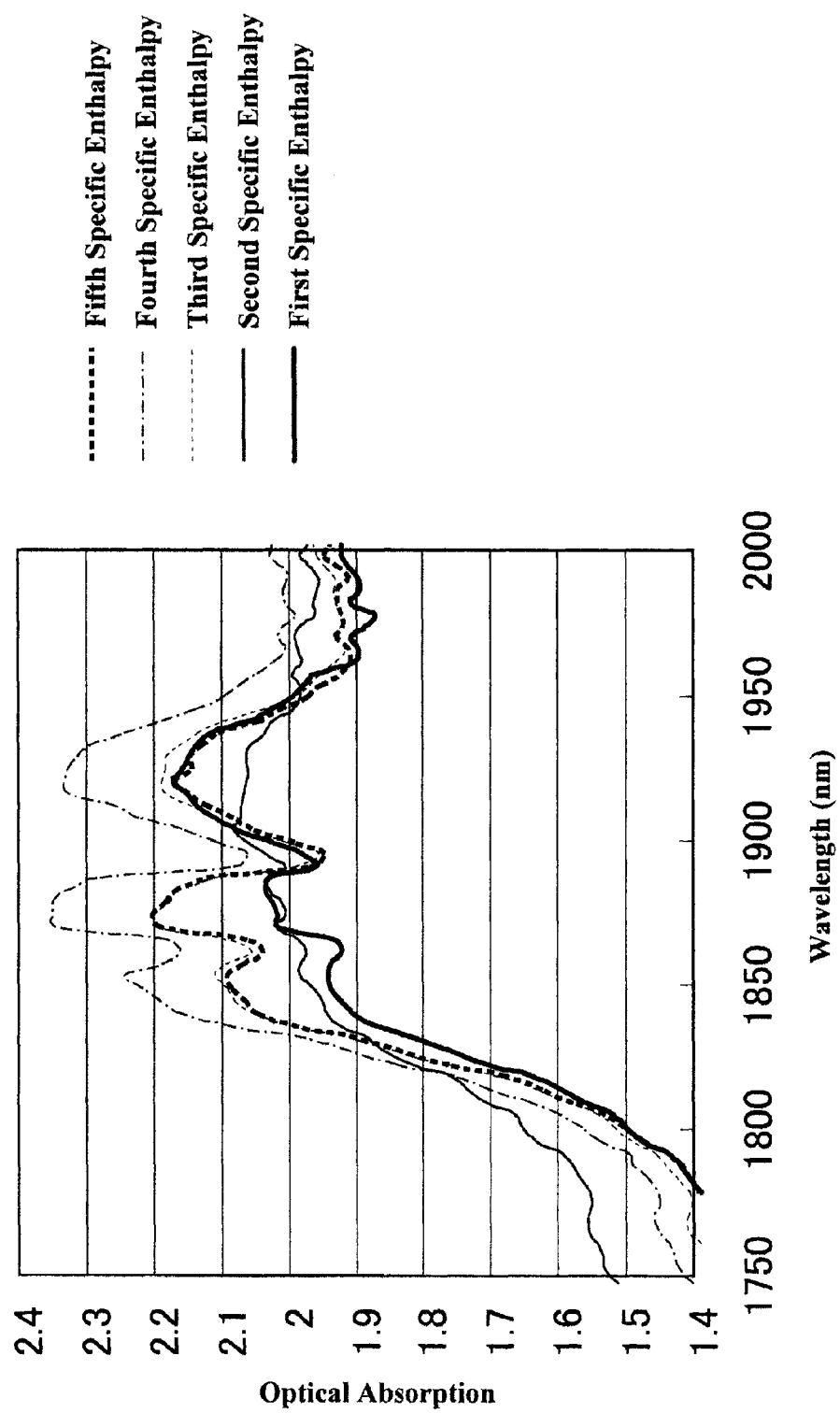
FIG. 10 is a graph illustrating an absorption spectrum according to an example.
Figure 11:
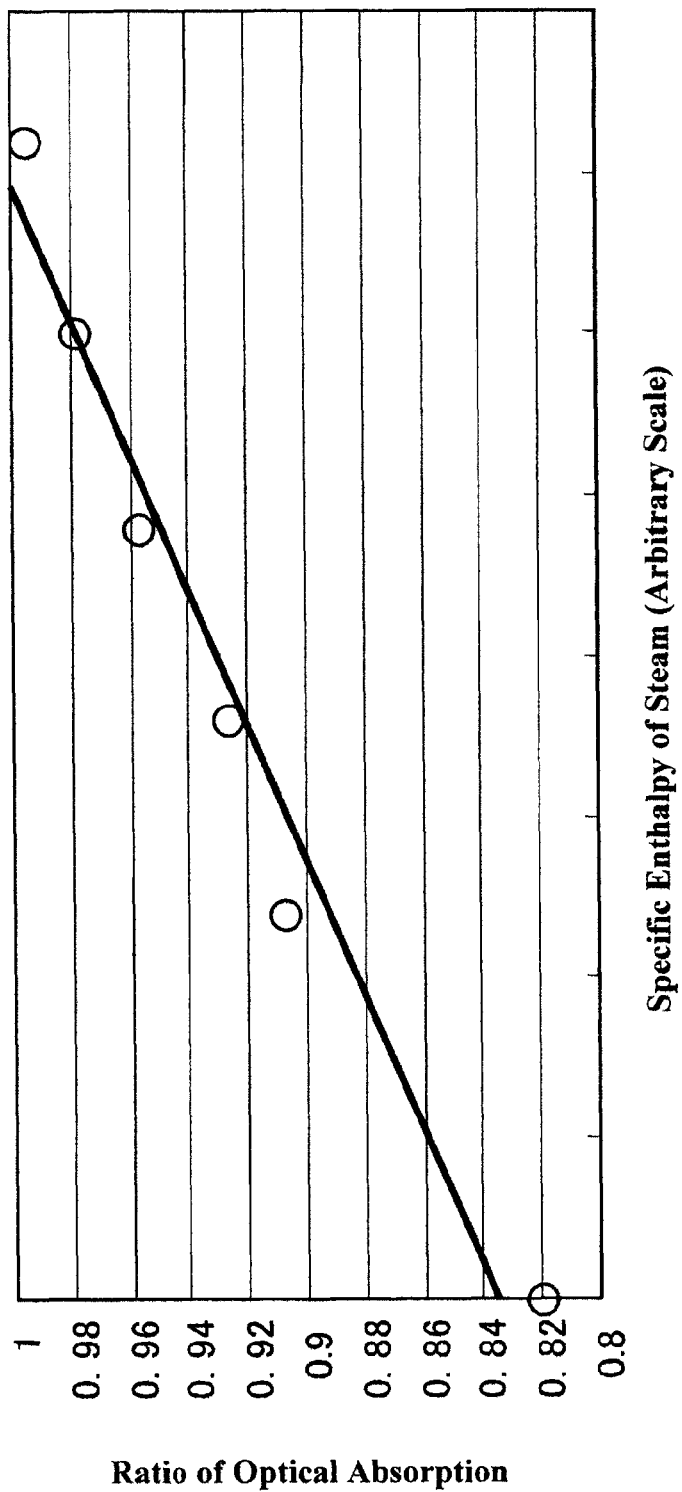
FIG. 11 is a graph illustrating the ratio of vapor relative enthalpy and optical absorption.

FIG. 10 is examples of a spectroscopic measurements of moist steam having first through fourth specific enthalpy is, and of superheated steam having a fifth specific enthalpy. The first specific enthalpy is the lowest, and the specific enthalpy of the steam was increased towards the fifth specific enthalpy through heating using a heater. FIG. 11 is a plot of the ratio R, calculated by the equation below, against the specific entropies of the steam, wherein $IS_0$ is the value of the integral of the absorption spectrum over the range of wavelengths from 1750 to 1770 nm, illustrated in FIG. 10, $IS_1$ is the value of the integral of the absorption spectrum over the range of wavelengths from 1870 to 1890 nm, and $IS_2$ is the value of the integral of the absorption spectrum over the range of wavelengths from 1910 to 1930 nm, $$R = (IS1 - IS0)/(IS2 - IS0) \quad (1)$$

The integral value IS0, for the absorption spectrum over the range wherein the wavelength is from 1750 to 1770 nm, is a part wherein there is no relationship to optical absorption by water, and has an effect of increasing or decreasing the absorption spectrum that is to be captured. The integral value 151, for the absorption spectrum over the range wherein the wavelength is from 1870 to 1890 nm, corresponds to the density of the water molecules that exist singly. The integral value 152, for the absorption spectrum over the range wherein the wavelength is from 1910 to 1930 nm, corresponds to the density of the water molecules wherein two molecules are bonded together by a single hydrogen bond.

As illustrated in FIG. 10, the higher the specific enthalpy of the steam, the higher the ratio R of the optical absorption. Consequently, a tendency is seen wherein the higher the specific enthalpy of the steam, the higher the ratio of density of the hydrogen molecules that exist singly relative to the density of the hydrogen molecules wherein two molecules are bonded together by one hydrogen bond.

Note that similar results can also be produced without using the integral values by plotting R, Obtained by Equation (2), against the specific enthalpy of the steam, when I0 is the optical absorption of light at a wavelength of 1760 nm, I1 is the optical absorption of light at a wavelength of 1880 nm, and I2 is the optical absorption of light at a wavelength of 1910 nm.

$$R = (I1 - I0)/(I2 - I0) \quad (2)$$

In Equation (1), the reason for taking the difference between IS1 and IS0 and the difference between IS2 and IS0 is to ensure that there is a single baseline for the optical spectrum. Consequently, in a case wherein there is no danger of variability in the baseline for the optical spectrum, the same results can be obtained through plotting, against the specific enthalpy of the steam, the ratio R of the integral value IS1 of the absorption spectrum over the wavelength range of 1870 to 1890 relative to integral value IS2 of the absorption spectrum over the wavelength range of 1910 to 1930, as given in Equation (3), below:

$$R = IS1/IS2 \quad (3)$$

Moreover similar results can also be produced without using the integral values by plotting R, obtained by Equation (4), against the specific enthalpy of the steam, when I1 is the optical absorption of light at a wavelength of 1880 nm, and I2 is the optical absorption of light at a wavelength of 1910 nm.

$$R = I1/I2 \quad (4)$$

The optical absorption ratio R is correlated to the ratio of water molecules existing singly, wherein no hydrogen bonds are formed, relative to clusters of water molecules wherein two water molecules are bonded together by one hydrogen bond. As described above, the average number of hydrogen bonds in a cluster falls as the dryness fraction moves from 0 to 1, where there tends to be an increase in the water molecules that exist singly. Consequently, the optical absorption ratio R tends to get larger as the dryness fraction approaches 1 from 0.

As illustrated in FIG. 1, a central calculation processing device (CPU) 300 is connected to the light-receiving element 12. The dryness fraction calculating portion 301 is included in the CPU 300. A data memory device 400 that includes a relationship memory portion 401 is connected to the CPU 300. The relationship memory portion 400 stores, for example, relationships obtained in advance between the optical absorption ratios R expressed in Equation (1) through Equation (4) and the dryness fraction. The relationship between the optical absorption ratio R and the dryness fraction may be stored as an equation, or may be stored as a table.

The dryness fraction calculating portion 301 calculates the dryness fraction of the moist steam based on a plurality of magnitude relationships between measured values of intensities of light that has traversed the moist steam at the respective plurality of wavelengths. For example, the dryness fraction calculating portion 301 receives, from the light-receiving element, an intensity spectrum for light that has traversed the moist steam within the pipe 21. Furthermore, the dryness fraction calculating portion 301 calculates the optical absorption spectrum due to the moist steam based on the optical intensity spectrum of the light prior to traversing the moist steam within the pipe 21 and the optical intensity spectrum of the light that has traversed the moist steam within the pipe 21. Moreover, the dryness fraction calculating portion 301 calculates the optical absorption ratio R as expressed by any of the aforementioned Equations (1) through (4) based on the absorption spectrum.

The dry fraction calculating portion 301 reads out, from the relationship memory portion 401, the relationship between the optical absorbing ratio R and the dryness fraction. The dryness fraction calculating portion 301 calculates the value for the moist steam within the pipe 21 based on the value for the optical absorbing ratio R that has been calculated and on the relationship between the optical absorbing ratio R and the dryness fraction.

Moreover, an inputting device 321, an outputting device 322, a program memory device 323, and a temporary memory device 324 are connected to the CPU 300. A switch, keyboard, or the like, may be used as the inputting device 321. The relationship between the optical absorption ratio R and the dryness fraction that is stored in the relationship memory portion 401 is inputted using, for example, the inputting device 321. An optical indicator, a digital indicator, a liquid crystal display device, or the like, may be used as the outputting device 322. The outputting device 322 displays, for example, a value for the moist steam within the pipe 21, calculated by the dryness calculating portion 301. The program memory portion 323 stores a program for executing, on the CPU 300, exchange of data between the devices that are connected to the CPU 300. The temporary memory device 324 stores data temporarily during the calculation processes of the CPU 300.

The dryness fraction measuring device according to the form of embodiment set forth above and the dryness fraction measuring method that uses the dryness fraction measuring device enable high accuracy measurements of moist steam dryness fractions, using an optical method, rather than using flow rate sensors and pressure sensors. Moreover, the dryness fraction calculating device according to the present form of embodiment does not require the provision of constriction valves or branched pipes within the pipes. Because of this, the drying fraction measuring device according to the present example of embodiment can be provided for a low cost. Furthermore, the conventional drying factor measuring device has a narrow measuring range, and for example, can perform measurements over a range of dryness fractions of only 0.9 to 1.0. In contrast, the dryness factor measuring device according to the conventional example is able to perform measurements over the entire range of dryness fractions, from 0 to 1.0, because the status of the water molecules can be viewed optically.

While there are descriptions of examples set forth above, the descriptions and drawings that form a portion of the disclosure are not to be understood to limit the present invention. A variety of alternate examples and operating technologies should be obvious to those skilled in the art. For example, an example of comparing the degree of absorption at the 1880 nm wavelength and the degree of absorption at the 1910 nm wavelength was described in the example of embodiment. Here the numerator and the denominator on the right-hand side of Equations (1) through (4) may be switched. Moreover, the optical absorption of the wavelength corresponding to the number of hydrogen bonds being zero and the optical absorption of the wavelength corresponding to the number of hydrogen bonds being two may be compared. Conversely, the optical absorption of the wavelength corresponding to the number of hydrogen bonds being zero and the optical absorption of the wavelength corresponding to the number of hydrogen bonds being three may be compared. Moreover, the optical absorption of the wavelength that is correlated to the number of hydrogen bonds being one and the optical absorption of the wavelength that is correlated to the number of hydrogen bonds being two may be compared, the optical absorption of the wavelength that is correlated to the number of hydrogen bonds being one and the optical absorption of the wavelength that is correlated to the number of hydrogen bonds being three may be compared, and the optical absorption of the wavelength that is correlated to the number of hydrogen bonds being two and the optical absorption of the wavelength that is correlated to the number of hydrogen bonds being three may be compared. In this way, the dryness fraction may be calculated based on the ratios of optical absorption means of an arbitrary plurality of wavelengths that are correlated to different numbers of hydrogen bonds. Conversely, a correlation may be established in advance between the dryness fraction and the differences between optical absorption means of an arbitrary plurality of wavelengths that are correlated to different numbers of hydrogen bonds, and the value for the dryness fraction may be calculated from the measured values for the differences between the optical absorptions of the plurality of wavelengths. The present invention should be understood to include a variety of forms of embodiment, and the like, not set forth herein.

The dryness fraction measuring device according to the present examples can be used in exposing the effects of increasing latent heat through a decompression valve, used in dryness fraction measurements for producing optimal boiler efficiency, used in steam turbine moisture loss measurements, used in optimal dryness fraction control of heat exchanging equipment, used in control of foodstuff manufacturing processes, such as in pasta making, used in the control of chemical processes, and the like.

The invention claimed is:

1. A dryness fraction measuring device, comprising:
a light-emitting body irradiating moist steam with light at a plurality of wavelengths;
a light-receiving element receiving light of a plurality of wavelengths that has traversed moist steam; and
a dryness fraction calculating portion calculating the dryness fraction of the moist steam based on a received light intensity of the light at each of the plurality of wavelengths;
wherein the dryness fraction calculating portion calculates the dryness fraction based on the received light intensities at two wavelengths; and
wherein of the two wavelengths, the optical absorption of light at one of the wavelengths is correlated to the density of water molecules that exist as single molecules in the moist steam, and the optical absorption of light at the other wavelength is correlated to the density of water molecules that form clusters of two molecules in the moist steam.

2. The dryness fraction measuring device as set forth in claim 1, wherein:
optical absorption of the light at each of the plurality of wavelengths is correlated with a number of hydrogen bonds formed between water molecules in a cluster.

3. The dryness fraction measuring device as set forth in claim 1, wherein:
the dryness fraction calculating portion calculates the dryness fraction based on a plurality of measured value magnitude relationships of the received light intensities of the light received at each of the plurality of wavelengths.

4. The dryness fraction measuring device as set forth in claim 1, wherein:
the dryness fraction calculating portion calculates the dryness fraction based on the ratio of received light intensities at two wavelengths.

5. The dryness fraction measuring device as set forth in claim 1, wherein:
the dryness fraction calculating portion calculates the dryness fraction based on the difference between received light intensities at two wavelengths.

6. The dryness fraction measuring device as set forth in claim 1, wherein:
the light-emitting body emits the light in a broad wavelength band, and is further provided with a wavelength filter.

7. A dryness fraction measuring method, comprising the steps of:
irradiating moist steam with light at a plurality of wavelengths;
receiving light of a plurality of wavelengths that has traversed the moist steam; and
calculating the dryness fraction of the moist steam based on a received light intensity of the light at each of the plurality of wavelengths;
wherein calculating the dryness fraction comprises the step of basing the calculation on the received light intensities at two wavelengths; and
wherein of the two wavelengths, the optical absorption of light at one of the wavelengths is correlated to the density of water molecules that exist as single molecules in the moist steam, and the optical absorption of light at the other wavelength is correlated to the density of water molecules that form clusters of two molecules in the moist steam.

8. The dryness fraction measuring method as set forth in claim 7, further comprising the step og:
correlating an optical absorption of the light at each of the plurality of wavelengths with a number of hydrogen bonds formed between water molecules in a cluster.

9. The dryness fraction measuring method as set forth in claim 7, wherein:
the dryness fraction is calculated based on a plurality of measured value magnitude relationships of the received light intensities of the light received at each of the plurality of wavelengths.

10. The dryness fraction measuring method as set forth in claim 7, wherein:
calculating the dryness fraction comprises the step of basing the calculation on the ratio of received light intensities at two wavelengths.

11. The dryness fraction measuring method as set forth in claim 7, wherein:

calculating the dryness fraction comprises the step of basing the calculation on the difference between received light intensities at two wavelengths.

* * * * *